US012564318B2

(12) United States Patent
Nakamura

(10) Patent No.: US 12,564,318 B2
(45) Date of Patent: Mar. 3, 2026

(54) SYSTEMS FOR REMOTELY CONTROLLING AN OPHTHALMOLOGICAL DEVICE

(71) Applicant: TOPCON CORPORATION, Tokyo (JP)

(72) Inventor: Satoshi Nakamura, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 336 days.

(21) Appl. No.: 18/251,302

(22) PCT Filed: Oct. 21, 2021

(86) PCT No.: PCT/JP2021/038971
§ 371 (c)(1),
(2) Date: May 1, 2023

(87) PCT Pub. No.: WO2022/091945
PCT Pub. Date: May 5, 2022

(65) Prior Publication Data
US 2023/0404389 A1 Dec. 21, 2023

(30) Foreign Application Priority Data
Nov. 2, 2020 (JP) ................................. 2020-183833

(51) Int. Cl.
| A61B 3/10 | (2006.01) |
| A61B 3/00 | (2006.01) |
| A61B 3/02 | (2006.01) |

(52) U.S. Cl.
CPC .............. *A61B 3/10* (2013.01); *A61B 3/0075* (2013.01); *A61B 3/0083* (2013.01); *A61B 3/02* (2013.01)

(58) Field of Classification Search
CPC ....... A61B 3/10; A61B 3/0075; A61B 3/0083; A61B 3/02
(Continued)

(56) References Cited

U.S. PATENT DOCUMENTS

| 9,931,171 B1 | 4/2018 | Peyman | |
| 2002/0003608 A1* | 1/2002 | Yamada ................. | A61B 3/185 |
| | | | 351/245 |

(Continued)

FOREIGN PATENT DOCUMENTS

| EP | 1568308 A1 * | 8/2005 | ............. G16H 40/67 |
| JP | H05253185 A1 | 10/1993 | |

(Continued)

OTHER PUBLICATIONS

Extended European Search Report mailed Aug. 13, 2024 in connection with European Patent Application No. 21886063.3, 8 pgs.

(Continued)

*Primary Examiner* — Sharrief I Broome
(74) *Attorney, Agent, or Firm* — Chiesa Shahinian & Giantomasi PC

(57) ABSTRACT

An ophthalmologic system includes an ophthalmologic apparatus including a measurement unit, a measurement information processor that converts measurement information measured by the measurement unit into image information and non-image information excluding the image information, an ophthalmologic apparatus display of the ophthalmologic apparatus that displays the image information, a terminal device that is disposed remotely from the ophthalmologic apparatus and includes a terminal display, a display imaging device that is attached to the ophthalmologic apparatus and captures an image of an entire screen shown on the ophthalmologic apparatus display, an image transmitter that transmits the image captured by the display imaging device to the terminal device, a measurement information transmitter of the ophthalmologic apparatus that transmits the measurement information to the terminal device, and an information integrator that integrates the (Continued)

image information transmitted from the image transmitter with the measurement information.

2 Claims, 5 Drawing Sheets

(58) Field of Classification Search
USPC ......................................................... 351/205
See application file for complete search history.

(56)                    References Cited

U.S. PATENT DOCUMENTS

| | | | | |
|---|---|---|---|---|
| 2003/0035084 A1* | 2/2003 | Makino | .................. | A61B 3/145 |
| | | | | 351/205 |
| 2010/0160789 A1 | 6/2010 | Dilworth et al. | | |
| 2017/0027445 A1* | 2/2017 | Isogai | ...................... | A61B 3/18 |
| 2018/0303667 A1 | 10/2018 | Peyman | | |
| 2020/0170506 A1 | 6/2020 | Higuchi | | |
| 2020/0245860 A1* | 8/2020 | Umano | ................ | A61B 3/0016 |
| 2022/0386869 A1* | 12/2022 | Ono | ........................ | G06V 40/19 |

FOREIGN PATENT DOCUMENTS

| | | | | |
|---|---|---|---|---|
| JP | 2006-280612 A | 10/2006 | | |
| JP | 2008048895 A | 3/2008 | | |
| JP | 2020-089408 A | 6/2020 | | |
| WO | WO-2013155002 A1 * | 10/2013 | ............. | G16H 30/20 |

OTHER PUBLICATIONS

International Search Report and Written Opinion mailed Jan. 18, 2022, in connection with International Patent Application No. PCT/JP2021/038971, 8 pgs. (including translation).
Office Action mailed Dec. 24, 2025, in connection with Chinese Patent Application No. 202180074156.2, 16 pgs. (including translation).

* cited by examiner

SYSTEMS FOR REMOTELY CONTROLLING AN OPHTHALMOLOGICAL DEVICE

CROSS-REFERENCE TO RELATED APPLICATION(S)

This application is a National Stage under 35 U.S.C. 371 of International Patent Application No. PCT/JP2021/038971, filed Oct. 21, 2021, which claims priority to Japanese Patent Application No. 2020-183833, filed Nov. 2, 2020; the disclosures of all of which are incorporated herein by reference in their entireties.

BACKGROUND

The present disclosure relates to an ophthalmologic system.

BACKGROUND ART

The recent pandemic outbreaks of infectious diseases have forced us to change our behavior and manner in the daily life completely, which have been also strongly required from the society and government to prevent the spread of infection. In particular, people are requested to avoid the "three Cs", which means that people should aggressively avoid closed and confined places with poor ventilation, crowded places with many people nearby, and close-contact settings where people can have close-range conversations. The "three Cs" should be required of course in hospitals much more.

Patent Document 1 discloses a known example of an ophthalmologic apparatus. Such an ophthalmologic apparatus may be placed in a room such as an examination room, which shall force an examiner, who may be a doctor, and a subject, who may be a patient taking an examination through the apparatus, to stay in the same room.

CITATION LIST

Patent Document

Patent Document 1: Japanese Unexamined Patent Publication No. 2006-280612.

SUMMARY OF THE INVENTION

Technical Problems

Considering the prevention of infectious diseases, it is unpreferable to have people in the same room or place that may be closed and confined as described above. Further, demand for telemedicine and remote medical care is increasing from the other viewpoints than the prevention of infectious diseases, and there are also needs for an ophthalmologic examination that can be performed with the examiner and the subject in different places remotely.

An object of the present disclosure is to provide an ophthalmologic system capable of appropriately conducting an ophthalmologic examination with an examiner and a subject in different places.

Solution to the Problems

To achieve the above-described object, the present disclosure provides an ophthalmologic system capable of remotely operating an ophthalmologic apparatus. The ophthalmologic system includes: an ophthalmologic apparatus including a measurement unit; a measurement information processor that converts measurement information measured by the measurement unit into image information and non-image information excluding the image information; an ophthalmologic apparatus display that shows the image information, of the ophthalmologic apparatus; a terminal device that is disposed remotely from the ophthalmologic apparatus and includes a terminal display; and a display imaging device that is attached to the ophthalmologic apparatus and captures an image of an entire screen shown on the ophthalmologic apparatus display; an image transmitter that transmits the image captured by the display imaging device to the terminal device; a measurement information transmitter of the ophthalmologic apparatus that transmits the measurement information to the terminal device; and an information integrator that integrates the image information transmitted from the image transmitter with the measurement information excluding the image information to show integrated information on the terminal display.

To achieve the above-described object, the present disclosure further provides a method for remotely operating an ophthalmologic apparatus. The method includes: measuring, by a measurement unit of the ophthalmologic apparatus, an eye of a subject to acquire measurement information; transmitting, by a measurement information transmitter, non-image information excluding image information from the measurement information acquired in the measuring, to a terminal device disposed in a remote place; capturing, by a display imaging device, an image of an entire screen shown on an ophthalmologic apparatus display of the ophthalmologic apparatus; transmitting, by an image transmitter, image information captured in the capturing, to the terminal device; and by an information integrator of the terminal device, integrating the received image information with the received non-image information and showing integrated information on a terminal display of the terminal device.

To achieve the above-described object, the present disclosure provides a program for remotely operating an ophthalmologic apparatus. The program causes a computer to execute: measuring, by a measurement unit of the ophthalmologic apparatus, an eye of a subject to acquire measurement information; transmitting, by a measurement information transmitter, non-image information excluding image information from the measurement information acquired in the measuring, to a terminal device disposed in a remote place; capturing, by a display imaging device, an image of an entire screen shown on an ophthalmologic apparatus display of the ophthalmologic apparatus; transmitting, by an image transmitter, image information captured in the capturing, to the terminal device; and by an information integrator of the terminal device, integrating the received image information with the received non-image information and showing integrated information on a terminal display of the terminal device.

Advantages of the Invention

The present disclosure allows an ophthalmologic examination to be appropriately conducted even when an examiner and a subject are in different places.

DESCRIPTION OF EMBODIMENTS

A general ophthalmologic apparatus is mainly configured to be used by a doctor or an examiner directly facing a patient or a subject, both of the doctor and the patient together in the same room such as a consultation room or an examination room, where the ophthalmologic apparatus shows the information on a display device provided as part of the ophthalmologic apparatus or a nearby display device connected to the ophthalmologic apparatus. Such a general apparatus is currently supposed to complete the examination in the same room, and basically has no function of transmitting the measurement information to a remote place.

Due to the recent pandemic of infectious diseases and the demands for telemedicine, future ophthalmologic apparatuses are expected to enable the remote examination, which allows an examiner in a room to measure an eye of a subject in a separate room or a remote place. However, the ophthalmologic apparatuses that have been already deployed in the market, commercially available, or being currently used have difficulties in having the remote control function.

One of the difficulties comes from that detailed measurement information, which the ophthalmologic apparatus should process, is prone to become too large to transmit to a remote place due to poor capability of information processing system of the existing ophthalmologic apparatus. In particular, image information included in the measurement information has an extremely large amount of data, which see difficulties to be transmitted to a remote place. The existing ophthalmologic apparatus at least spends long time to process and transmit such image information, which hinders real-time examination with the remote place. In view of the foregoing background, which is merely one of the triggers for the present disclosure, studies have been made on an ophthalmologic system which allows the examiner to measure an eye of the subject as the examiner currently does with the known art, as well as allows the examiner to check the information remotely and in real-time manner by acquisition of image information, and recombination of the measurement information and the image information in a remote place.

(Configuration of System)

Figure 1:
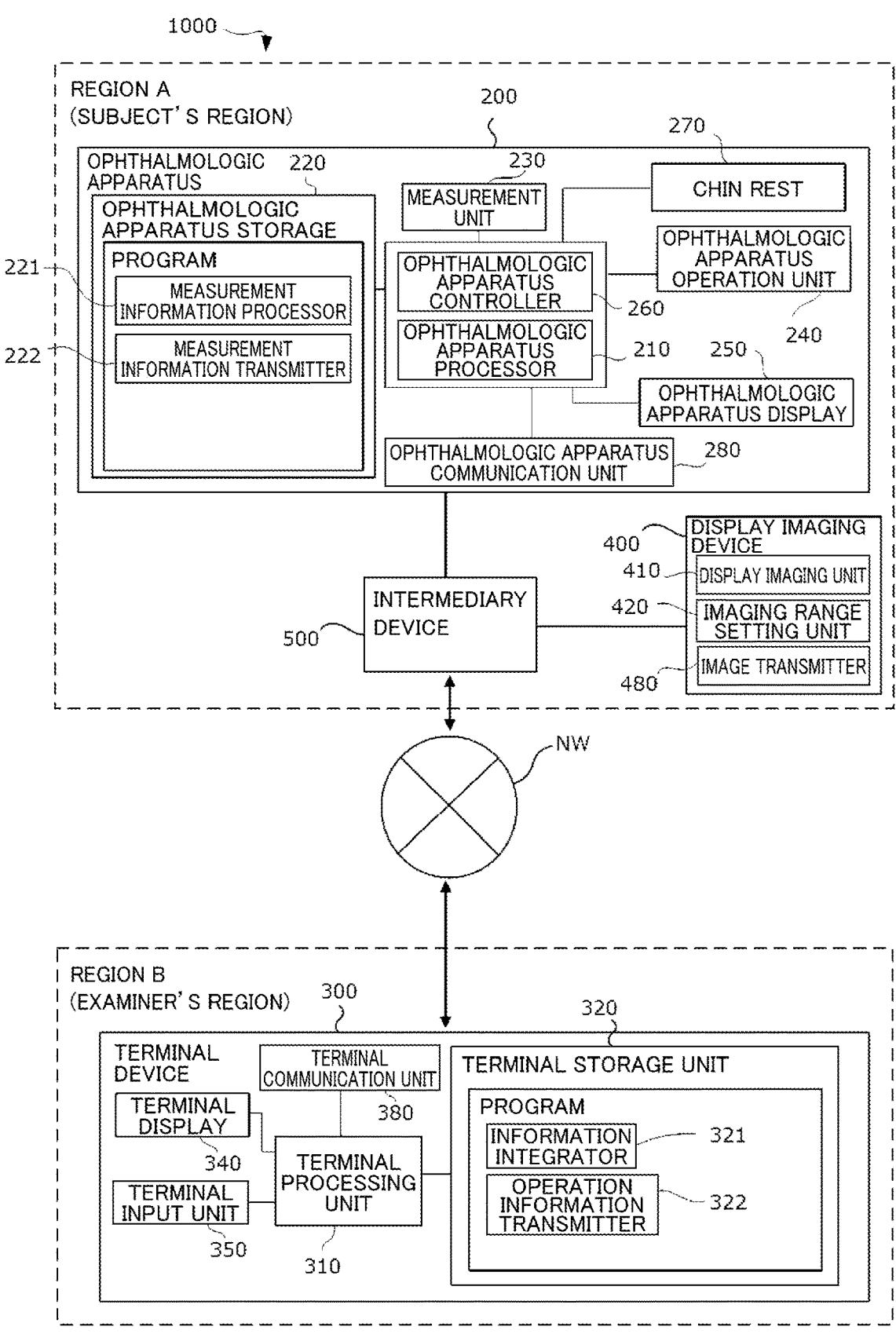
FIG. 1 is a view of a configuration of an ophthalmologic system of an embodiment of the present disclosure.
Figure 2:
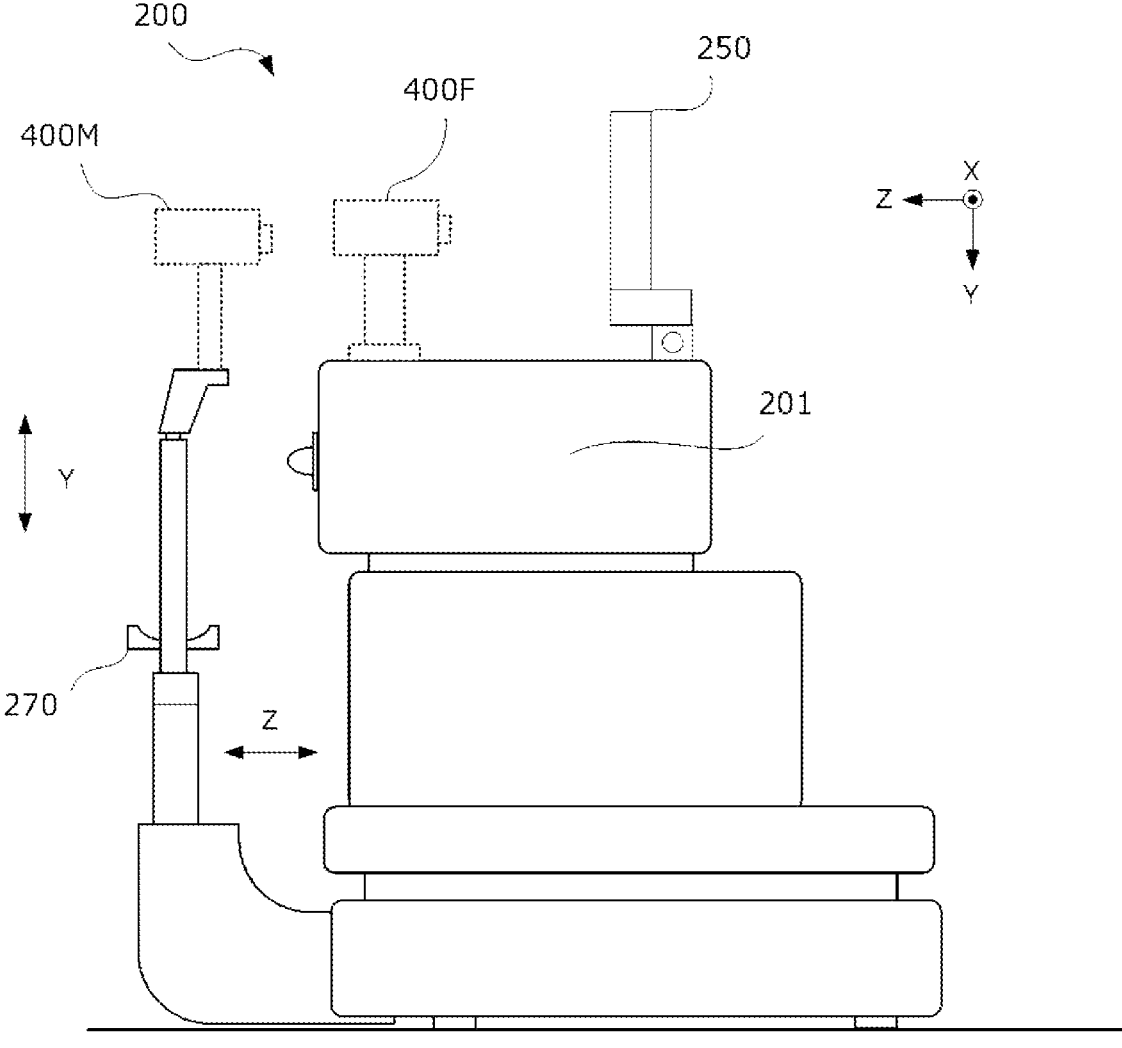
FIG. 2 is a view of an ophthalmologic apparatus.

Embodiments of the present disclosure will be described below with reference to the drawings. FIG. 1 is a configuration diagram of an ophthalmologic system of the present disclosure, and FIG. 2 is a view of an ophthalmologic apparatus that is a part of the ophthalmologic system.

The ophthalmologic system 1000 mainly has a region A where a subject resides (subject's region) and a region B where an examiner resides (examiner's region), and includes a network NW that connects the two regions for information communications.

The region A where the subject resides is provided with an ophthalmologic apparatus 200 that measures an eye of the subject, and a display imaging device 400 that captures images to show an entire ophthalmologic apparatus display 250 of the ophthalmologic apparatus 200. The region A may be further provided with an intermediary device 500 that intermediates the communication between the ophthalmologic apparatus 200 and the network NW. The measurement information of the subject's eye measured in the region A is transmitted to the region B via the network NW.

The region B where the examiner resides is provided with a terminal device 300, which allows the examiner to check the measurement information received from the region A and remotely operate the ophthalmologic apparatus 200 from the region B.

The network NW is a communication network that connects the apparatus and the devices in the regions A and B and is capable of transmitting and receiving data. The network NW may be implemented with, for example, part of the Internet, an intranet, a virtual private network, a local area network, a telephone network, LTE, 5G, Bluetooth (registered trademark), or satellite communications, and may be implemented with wired communication or wireless communication.

The ophthalmologic apparatus 200 includes an ophthalmologic apparatus processor 210, an ophthalmologic apparatus storage 220, a measurement unit 230, an ophthalmologic apparatus operation unit 240, an ophthalmologic apparatus display 250, an ophthalmologic apparatus controller 260, a chin rest 270, and an ophthalmologic apparatus communication unit 280.

Examples of the ophthalmologic apparatus 200 may include an auto kerato refractometer, a visual acuity examination device, a refractor head, an ophthalmologic apparatus including the visual acuity examination device or the refractor head, other a subjective examination apparatus, an refractometer, a corneal topography apparatus, a fundus imaging apparatus, an eye axial length measurement apparatus, a tonometer, a specular microscope, a slit lamp, an optical coherence tomography (OCT) apparatus, and a scanning laser ophthalmoscope (SLO).

The ophthalmologic apparatus processor 210 is a central processing unit, and executes functions and/or methods implemented by codes or commands included in programs stored in the ophthalmologic apparatus storage 220. The ophthalmologic apparatus processor 210 may include, for example, a central processing unit (CPU), a microprocessor unit (MPU), a graphics processing unit (GPU), a microprocessor, a processor core, a multiprocessor, an application specific integrated circuit (ASIC), and a field-programmable gate array (FPGA), and may achieve processes disclosed in the embodiment by a logic circuit or a dedicated circuit formed in an integrated circuit.

The ophthalmologic apparatus storage 220 stores various programs and data that are necessary. The ophthalmologic apparatus storage 220 can also store measurement information acquired by the measurement unit 230 and information calculated based on the measurement information. The ophthalmologic apparatus storage 220 is any of various types of storage media such as a hard disk drive (HDD), a solid state drive (SSD), and a flash memory. The ophthalmologic apparatus storage 220 also stores a measurement information processor 221 and a measurement information transmitter 222 as programs.

The measurement unit 230 measures the subject's eye. The position of the measurement unit 230 can be controlled by the ophthalmologic apparatus controller 260. The measurement unit 230 can be controlled to move in a horizontal direction (X and Z directions) and a vertical direction (Y direction) perpendicular to the horizontal direction, as X, Y and Z directions are shown in FIG. 2.

The ophthalmologic apparatus operation unit 240 is an operation device to operate the ophthalmologic apparatus 200 including moving the measurement position of the measurement unit 230. The ophthalmologic apparatus operation unit 240 may be implemented with a touchscreen integrated with the ophthalmologic apparatus display 250, for example, which allows the examiner to operate by touching the screen. Alternatively, the ophthalmologic apparatus operation unit 240 can be implemented with an operating lever or button attached to the ophthalmologic apparatus 200. A user's operation to the ophthalmologic apparatus operation unit 240 is transmitted to the ophthalmologic apparatus controller 260 to adjust the position of the measurement unit 230, for example.

The ophthalmologic apparatus display 250 may be implemented with a liquid crystal display, or a touchscreen showing operation buttons and an image of the subject's eye, which has been captured and measured with the ophthalmologic apparatus 200. The ophthalmologic apparatus display 250 is installed to move rotatably about a horizontal axis (about an X-axis or a Z-axis) and a vertical axis (about a Y-axis) and can be manually angled or oriented as appropriate when the remote control is not required. During the remote control, on the other hand, the ophthalmologic apparatus display 250 is preferably fixed in an orientation and position that allow the display imaging device 400 to capture an image of the entire screen of the ophthalmologic apparatus display 250.

The ophthalmologic apparatus controller 260 controls the positions of the measurement unit 230 and the chin rest 270. The ophthalmologic apparatus controller 260 is implemented with a position controller, which receives operation information from the ophthalmologic apparatus operation unit 240 to move movable components of the ophthalmologic apparatus 200, such as the measurement unit 230 and the chin rest 270. For example, the ophthalmologic apparatus controller 260 can move the movable components along the X, Y, and Z directions by a predetermined moving amount at a predetermined moving speed in accordance with the operation information.

The chin rest 270, which is connected to the body of the ophthalmologic apparatus 200 and support the chin and face of the subject, can be driven in the X, Y, and Z directions. The chin rest 270 may include a forehead rest that supports the forehead of the subject. The chin rest 270 is not necessarily directly support the chin as long as the subject's eye is fixed during the measurement. The ophthalmologic apparatus controller 260 controls the driving of the chin rest 270 so that the chin rest 270 receives the chin of the subject at an appropriate position.

The ophthalmologic apparatus communication unit 280 can communicate to the terminal communication unit 380 of the terminal device 300 in a remote place via the network NW, and can transmit the measurement information obtained by the measurement of the subject's eye by the ophthalmologic apparatus 200. The communication may be implemented by any communication protocol, in any of wired or wireless manner.

The display imaging device 400 includes a display imaging unit 410, an imaging range setting unit 420, and an image transmitter 480.

The display imaging device 400 may be implemented with a so-called Web camera, live camera, or real-time camera, to transmit a moving or still image captured by the display imaging unit 410 to the terminal device 300 in real time by the image transmitter 480. The display imaging device 400 may be connected to the intermediary device 500 via, for example, a USB cable and a USB connector.

The display imaging device 400 may include the imaging range setting unit 420. The display imaging unit 410 may include, for example, zoom-in and zoom-out functions, which allows the display imaging unit 410 to adjust the imaging range as such, via the connected intermediary device 500 and the remote terminal device 300.

FIG. 2 shows examples of attachment positions of the display imaging device 400, in which display imaging devices 400F and 400M drawn with dotted lines indicate the attachment positions.

When attached on a place indicated as the display imaging device 400F, the display unit imaging apparatus 400 will be installed to one of the places that keep fixed distances away from the ophthalmologic apparatus display 250, such as a place on a housing 201 of the ophthalmologic apparatus 200. This place, indicated as the display imaging device 400F, allows the display imaging device 400 to capture an image of the entire ophthalmologic apparatus display 250 at a fixed position even when the measurement unit 230 moves to any place according to the ophthalmologic apparatus controller 260.

When attached on a place indicated as the display imaging device 400M, the display imaging device 400 will be installed to one of the places that have varying distances from the ophthalmologic apparatus display 250, such as a place on the chin rest 270. This place, indicated as the display imaging device 400M, allows the display imaging device 400 to capture an image of the entire ophthalmologic apparatus display 250 from any position in a movable range of the chin rest 270. More specifically, the display imaging device 400 attached on a place indicated as the display imaging device 400M is configured by changing the attachment position or the imaging range of the display imaging device 400 with the imaging range setting unit 420 depending on the attachment position to capture the image of the entire ophthalmologic apparatus display 250.

Thus, these configurations allow the display imaging device 400 to capture the image of the entire ophthalmologic apparatus display 250 at any of the attachment positions indicated as the display imaging devices 400F and 400M. The preference to choose either of the attachment positions indicated as the display imaging devices 400F and 400M depends on the specific configuration of the ophthalmologic apparatus 200 to which the display imaging device is applied.

The intermediary device 500 may be implemented with any communication device such as a general-purpose computer or a router, which connects the ophthalmologic apparatus 200 and the display imaging device 400 to the network NW.

The terminal device 300 includes a terminal processing unit 310, a terminal storage unit 320, a terminal display 340, a terminal input unit 350, and a terminal communication unit 380.

Examples of the terminal device 300 include commercially available devices, such as a general-purpose computer, a desktop personal computer (PC), a laptop PC, a smartphone, a tablet PC, a handheld computer device, and a wearable terminal (e.g., an eyeglass-type device, a direct retinal projection device, a virtual reality (VR) terminal integrated with a head-mounted display, and a mixed reality (MR) terminal). These commercially available terminals in which certain pieces of application software are installed can be used as the terminal device 300 of the present embodiment.

The terminal processing unit 310 is a central processing unit, and executes functions and/or methods implemented by codes or commands included in the programs stored in the ophthalmologic apparatus storage 220. The terminal processing unit 310 may include, for example, a central processing unit (CPU), an MPU, a GPU, a microprocessor, a processor core, a multiprocessor, an ASIC, and an FPGA, and may achieve processes disclosed in the embodiment by a logic circuit or a dedicated circuit formed in an integrated circuit.

The terminal storage unit 320 stores various programs and data that are necessary. The terminal storage unit 320 is any of various types of storage media such as an HDD, an SSD, and a flash memory. The terminal storage unit 320 also stores an information integrator 321 and an operation information transmitter 322 as programs.

The terminal display 340 is implemented with any one or a combination of all types of devices capable of displaying a screen. The terminal display 340 includes, for example, a flat display such as a liquid crystal display or an organic light-emitting diode (OLED display), a curved display, or a device capable of projecting images onto a substance using a projector.

A terminal input unit 350 is a device that allows a user to input or select information, such as a keyboard, a mouse, or a touchpad. The input and selection of information includes inputting of numerical values, characters, or symbols, or selecting an item or process among options. The terminal input unit 350 may be implemented with a touchscreen integrated with a display 212 of a smartphone, a tablet, or a liquid crystal display or organic EL display of a PC. The input unit 211 may be a voice input device. The terminal input unit 350 may be a panel or a button that appears on the screen of the terminal display 340 operated by the hardware device.

The terminal communication unit 380 can communicate to the ophthalmologic apparatus communication unit 280 of the ophthalmologic apparatus 200 as well as the display imaging device 400 in a remote place via the network NW, and can receive measurement information obtained by measuring the subject's eye from the ophthalmologic apparatus 200 and image information about the image of the entire ophthalmologic apparatus display 250 from the display imaging device 400. The communication may be implemented by any communication protocol, in any of wired or wireless manner.

(Process Flow)

Figure 3:
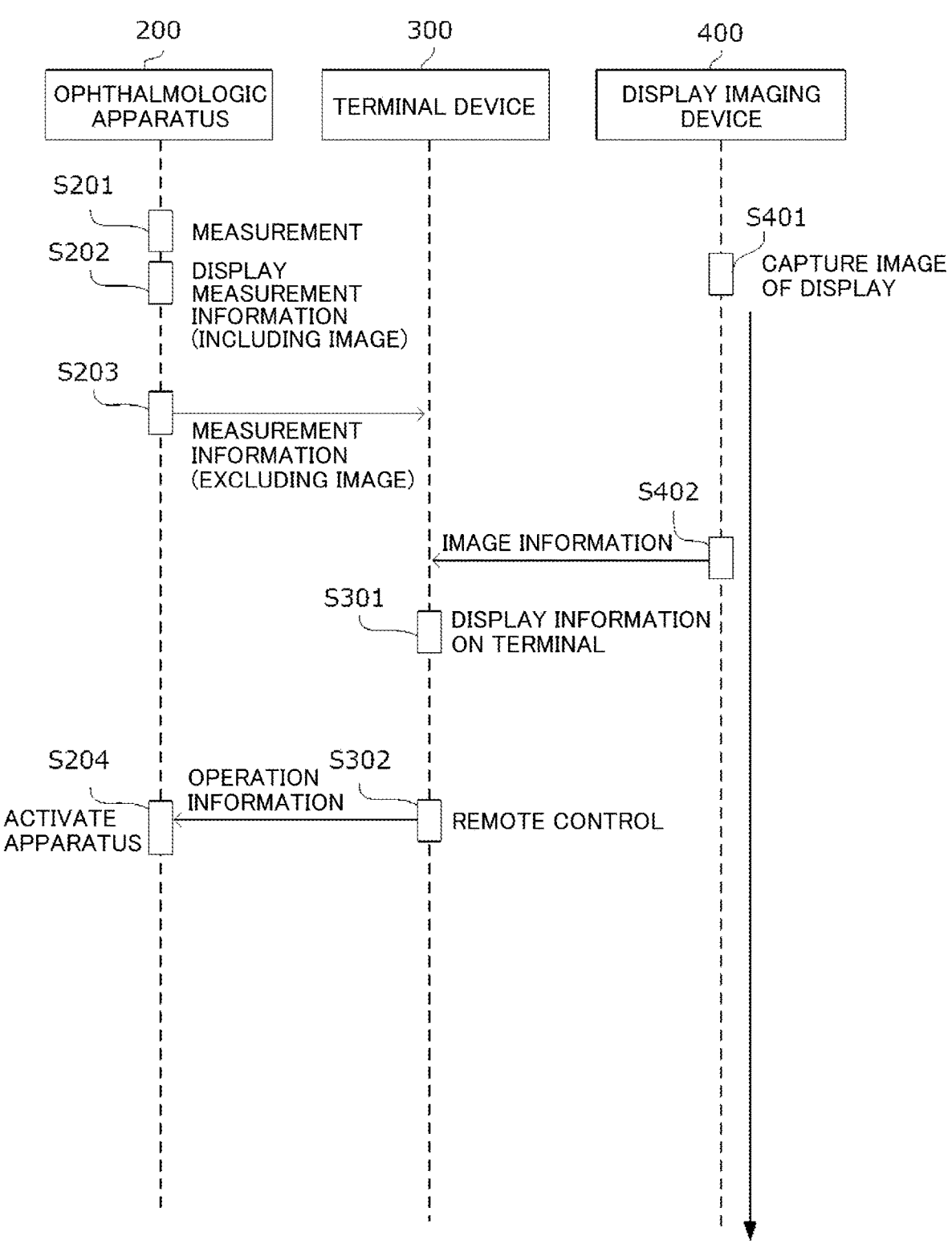
FIG. 3 is a sequence diagram illustrating a process flow of the present embodiment.

FIG. 3 is a sequence diagram illustrating a process flow of the ophthalmologic system and a method for remotely operating the ophthalmologic system according to the embodiment of the present disclosure. This drawing illustrates the processes of the ophthalmologic apparatus 200, the terminal device 300, and the display imaging device 400 in chronological order.

An exemplary embodiment will be described below in which the examiner in the region B remotely measures the eye of the subject in the region A, which is apart from region B. Note that the term "remote" in the present disclosure does not necessarily mean that there should have a certain distance or more between the examiner and the subject, but also means that they reside in a shorter distance such that the examiner and the subject can be in different rooms in the same building, for example.

First, in Step S201, the measurement unit 230 of the ophthalmologic apparatus 200 measures the eye of the subject to acquire measurement information. Specifically, when the ophthalmologic apparatus 200 is turned on and activated, and the subject puts his or her chin on the chin rest 270 in Step S201, the ophthalmologic apparatus controller 260 controls the chin rest 270 to move to an appropriate position. Then, when the position of the chin rest 270 is ready for measuring the eye of the subject, the measurement unit 230 captures an image to acquire various kinds of measurement information. Additionally, the region A can be further provided with a camera or an image capturing device to capture the image of the subject and the measurement for the examiner, and the region A and B can be further provided with audio-visual equipment such as a microphone, a speaker and a display, which allows a voice instruction to give from a remote place, or to show an instruction on the display when no supporting person is present for the subject in the region A.

In Step S202, based on the measurement information acquired by the measurement unit 230, the ophthalmologic apparatus processor 210 processes the measurement information to produce and show image information on the ophthalmologic apparatus display 250.

Figure 4:
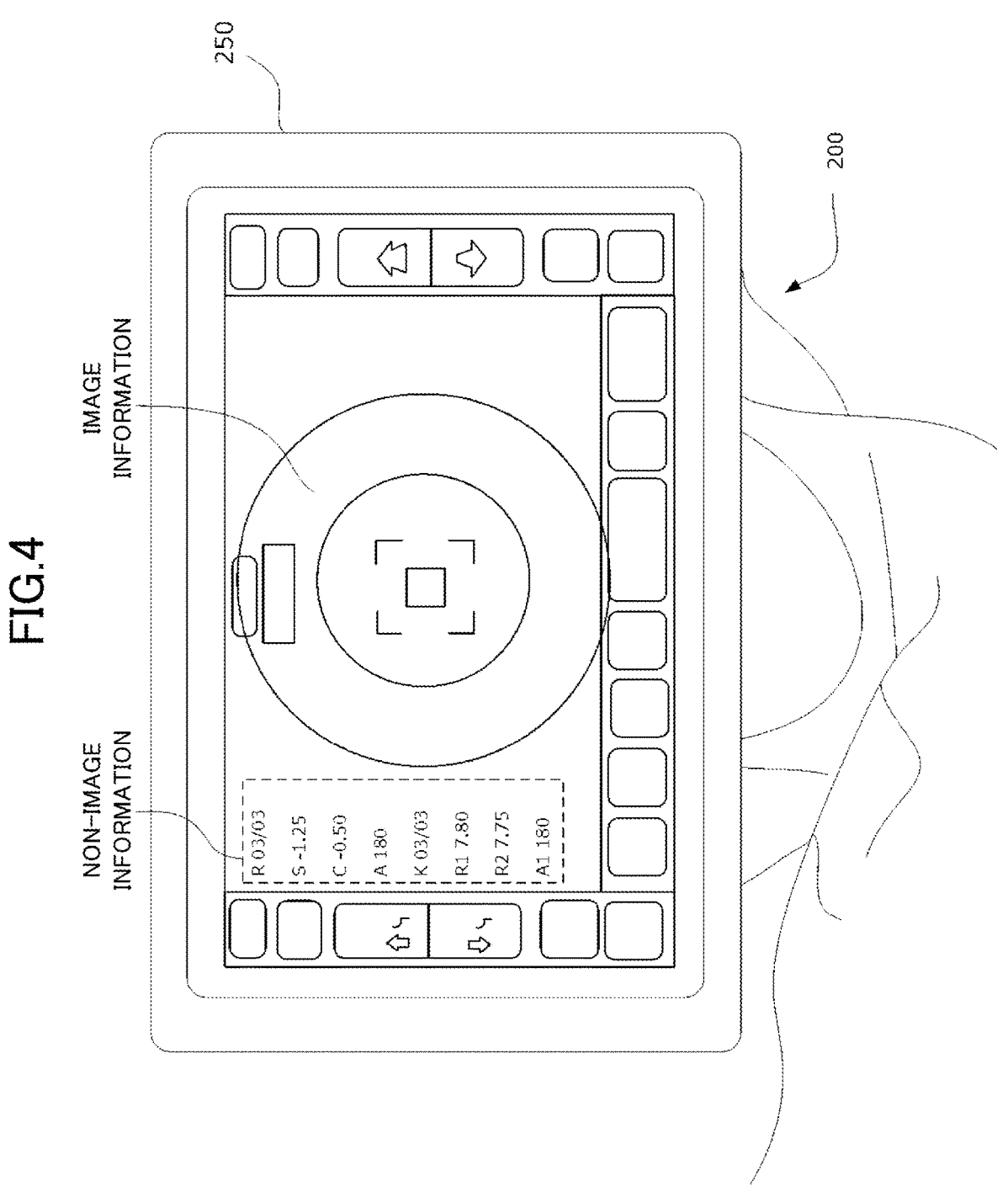
FIG. 4 is a view of an example image shown on an ophthalmologic apparatus display.

FIG. 4 is an example view of the image shown on the ophthalmologic apparatus display 250. The image shown at the center of the ophthalmologic apparatus display 250 is the eye of the subject, and the non-image information shown beside the image information and enclosed by a dotted rectangle is various items of numerical information calculated from the image information. The non-image information further includes the coordinates at which the measurement is being carried out, information about a mode of the measurement of the ophthalmologic apparatus 200, and patient information about a subject who is the target of the measurement.

In Step S401, the display imaging unit 410 of the display imaging device 400 captures an image of the entire screen of the ophthalmologic apparatus display 250 of the ophthalmologic apparatus 200. The display imaging device 400 basically keeps capturing during the measurement, which is illustrated by a down-side arrow just below S401 in FIG. 3 for convenience's sake.

In Step S402, the image transmitter 480 transmits the image information captured by the display imaging unit 410 to the terminal device 300 via the network NW. This step also keeps continuing in the same manner as Step S401.

In Step S203, the measurement information transmitter 222 transmits the non-image information, excluding the image information from the measurement information acquired by the measurement unit 230, to the remote terminal device 300. The non-image information excluding the image information from the measurement information is the numerical information shown in FIG. 4, and the measurement information processor processes the non-image information in the same manner as even under the remote control and the non-remote control to show on the ophthalmologic apparatus display 250. Transmitting the non-image information alone excluding the image information to the terminal device 300 can reduce the processing load on the ophthalmologic apparatus processor 210 and improve the real-time manner of the measurement.

In Step S301, the information integrator 321 integrates the image information received from the display imaging device 400 with the non-image information received from the ophthalmologic apparatus 200 to show the integrated information on the terminal display 340 of the terminal device 300.

Figure 5:
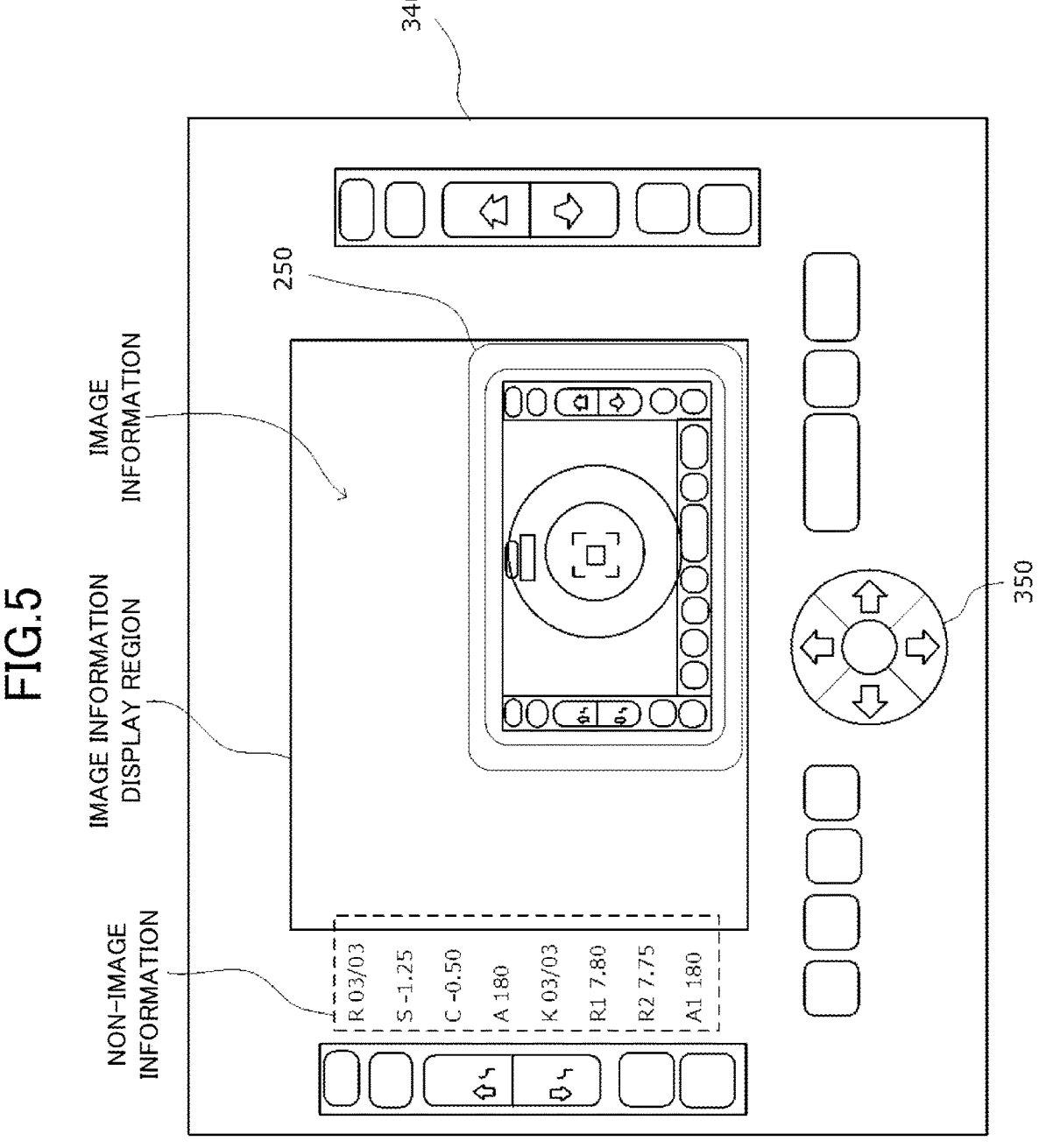
FIG. 5 is a view of an example image shown on a terminal display.

FIG. 5 is an example view of the image shown on the terminal display 340. The image shown in an image information display region at the center of the screen is the image information captured and transmitted by the display imaging device 400. The non-image information shown beside the image information is the measurement information excluding the image information acquired and transmitted from the ophthalmologic apparatus 200. The terminal input unit 350 for remotely operating the ophthalmologic apparatus 200 is shown in the form of buttons or panels on the screen. Such a screen can be implemented by using a Web browser function installed in the terminal device 300.

Thus, the information integrator 321 can integrate the transmitted image information and non-image information together to show the integrated information on the terminal display 340. This allows the examiner in the region B to use the ophthalmologic apparatus 200 in the region A, which is apart from the region B, as if the examiner were in the region A directly operating the ophthalmologic apparatus 200 in the region A.

In this drawing, the image information display region is not entirely but partially occupied with an image of the ophthalmologic apparatus display 250, and the remaining part of the region is shown as a blank part. This example illustrates that the display imaging device 400 is configured to capture the image of the entire ophthalmologic apparatus display 250 even though the display imaging device 400 is installed to one of the places indicated as the display imaging device 400M shown in FIG. 2, the places have varying distances from the ophthalmologic apparatus display 250. Consequently, the image information display region can be configured with the display imaging device 340 to show the entire ophthalmologic apparatus display 250 with or without the blank part, even though the display imaging device 400M is installed on any place of its movable range.

A process flow for remotely operating the ophthalmologic apparatus 200 will be described below. In Step S302, when the examiner operates the terminal device 300 through the terminal input unit 350, the operation information transmitter 322 produces operation information corresponding to the operation to the ophthalmologic apparatus 200 to transmits to the ophthalmologic apparatus 200. The operation information, specifically, can be produced from some inputs of the examiner's operation through some hardware devices including a mouse and/or a keyboard for some virtually produced operation units including software buttons and/or panels shown on the screen of FIG. 5, for example. While the face-to-face measurement uses a touchscreen installed as the ophthalmologic apparatus display 250 to specify the target to measure where the pupil is in the eye of the subject, the remote measurement disclosed in this embodiment uses a Web browser, for example, to show the pupil of the subject on the screen to specify its position by clicking with the mouse.

In Step S204, the ophthalmologic apparatus controller 260 allows the components of the ophthalmologic apparatus 200 to control in accordance with the operation information, which has been received from the terminal device 300.

As described above, according to the embodiment of the present disclosure, the ophthalmologic system includes the ophthalmologic apparatus 200 including the measurement unit 230, the measurement information processor 221 that converts the measurement information measured by the measurement unit 230 into image information and non-image information excluding the image information, the ophthalmologic apparatus display 250 of the ophthalmologic apparatus 200 that shows the image information, the terminal device 300 that is disposed remotely from the ophthalmologic apparatus 200 and includes the terminal display 340, the display imaging device 400 that is attached to the ophthalmologic apparatus 200 and captures an image of an entire screen shown on the ophthalmologic apparatus display 250, the image transmitter 480 that transmits the image captured by the display imaging device 400 to the terminal device 300, the measurement information transmitter 222 of the ophthalmologic apparatus 200 that transmits the measurement information to the terminal device 300, and the information integrator 321 that integrates the image information transmitted from the image transmitter 480 with the measurement information excluding the image information to show the integrated information on the terminal display 340. This configuration can reduce the processing load on the ophthalmologic apparatus by transmitting the image information via a different route, and the state of the measurement can be successively checked, allowing an appropriate ophthalmologic examination although the examiner and the subject are in different spaces.

The operation information transmitter 322 produces operation information, which is corresponding to the operation of the ophthalmologic apparatus 200 based on the information inputted via the terminal input unit 350 of the terminal device 300, to transmits the operation information to the ophthalmologic apparatus 200, and the ophthalmologic apparatus controller 260 controls the driving of the ophthalmologic apparatus 200 based on the operation information received from the operation information transmitter 322. Thus, although the examiner and the subject are in different spaces, the ophthalmologic apparatus can be operated by remote control using the terminal device 300 as if the examiner and the subject are in the same space.

The ophthalmologic apparatus 200 includes the chin rest 270 that is driven to receive the subject's chin at an appropriate position, the ophthalmologic apparatus controller 260 controls the driving of the chin rest 270, and the display imaging device 400 is at a position where the display imaging device can capture the image of the entire ophthalmologic apparatus display 250 and is not driven by the ophthalmologic apparatus controller 260. This allows the examiner to receive the whole image information obtained from the ophthalmologic apparatus display 250 and measure the subject's eye appropriately.

The ophthalmologic apparatus 200 includes the chin rest 270 that is driven to receive the subject's chin at an appropriate position, the ophthalmologic apparatus controller 260 controls the driving of the chin rest 270, the display imaging device 400 is attached to the chin rest 270, and the imaging range of the display imaging device 400 is set such that the display imaging device can capture the image of the entire ophthalmologic apparatus display 250 at any position in a driving range of the chin rest 270. This allows the examiner to receive the whole image information obtained from the ophthalmologic apparatus display 250 and measure the subject's eye appropriately.

The embodiments of the present disclosure, which have been described above, do not limit the aspects of the present disclosure to these embodiments.

DESCRIPTION OF REFERENCE CHARACTERS

200 Ophthalmologic Apparatus
201 Housing
210 Ophthalmologic Apparatus Processor
220 Ophthalmologic Apparatus Storage
221 Measurement Information Processor
222 Measurement Information Transmitter
230 Measurement Unit
240 Ophthalmologic Apparatus Operation Unit
250 Ophthalmologic Apparatus Display
260 Ophthalmologic Apparatus Controller
270 Chin Rest
280 Ophthalmologic Apparatus Communication Unit

300 Terminal Device
310 Terminal Processing Unit
320 Terminal Storage Unit
321 Information Integrator
322 Operation Information Transmitter
340 Terminal Display
350 Terminal Input Unit
380 Terminal Communication Unit
400 Display Imaging Device
410 Display Imaging Unit
420 Imaging Range Setting Unit
480 Image Transmitter
500 Intermediary Device
1000 Ophthalmologic System
NW Network

The invention claimed is:

1. An ophthalmologic system capable of remotely operating an ophthalmologic apparatus, the ophthalmologic system comprising:

an ophthalmologic apparatus including a measurement unit;

a measurement information processor that converts measurement information measured by the measurement unit into image information and non-image information excluding the image information;

an ophthalmologic apparatus display of the ophthalmologic apparatus that shows the image information;

a terminal device that is disposed remotely from the ophthalmologic apparatus and includes a terminal display;

a display imaging device that is attached to the ophthalmologic apparatus and captures an image of an entire screen shown on the ophthalmologic apparatus display;

an image transmitter that transmits the image captured by the display imaging device to the terminal device;

a measurement information transmitter of the ophthalmologic apparatus that transmits the measurement information to the terminal device; and an information integrator that integrates the image information transmitted from the image transmitter with the measurement information excluding the image information to show integrated information on the terminal display, wherein the ophthalmologic apparatus includes a chin rest that is driven to receive a chin of a subject at an appropriate position;

the ophthalmologic apparatus controller controls driving of the chin rest, and the display imaging device is at a position where the display imaging device is able to capture an image of the entire ophthalmologic apparatus display and is not driven by the ophthalmologic apparatus controller.

2. An ophthalmologic system capable of remotely operating an ophthalmologic apparatus, the ophthalmologic system comprising:

an ophthalmologic apparatus including a measurement unit;

a measurement information processor that converts measurement information measured by the measurement unit into image information and non-image information excluding the image information;

an ophthalmologic apparatus display of the ophthalmologic apparatus that shows the image information;

a terminal device that is disposed remotely from the ophthalmologic apparatus and includes a terminal display;

a display imaging device that is attached to the ophthalmologic apparatus and captures an image of an entire screen shown on the ophthalmologic apparatus display;

an image transmitter that transmits the image captured by the display imaging device to the terminal device;

a measurement information transmitter of the ophthalmologic apparatus that transmits the measurement information to the terminal device; and an information integrator that integrates the image information transmitted from the image transmitter with the measurement information excluding the image information to show integrated information on the terminal display, wherein the ophthalmologic apparatus includes a chin rest that is driven to receive a chin of a subject at an appropriate position;

the ophthalmologic apparatus controller controls driving of the chin rest, and the display imaging device is attached to the chin rest; and an imaging range of the display imaging device is set such that the display imaging device is able to capture an image of the entire ophthalmologic apparatus display at any position in a driving range of the chin rest.

* * * * *